(12) United States Patent
Yamazaki et al.

(10) Patent No.: US 7,361,278 B2
(45) Date of Patent: Apr. 22, 2008

(54) PROCESS FOR PRODUCING MASS TRANSFER DEVICE AND APPARATUS FOR PRODUCTION THEREOF

(75) Inventors: Takeo Yamazaki, Yokohama (JP); Naoto Mihashi, Tokyo (JP); Takeshi Imamura, Chigasaki (JP); Satoko Omizu, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 406 days.

(21) Appl. No.: 11/030,289

(22) Filed: Jan. 7, 2005

(65) Prior Publication Data
US 2005/0121378 A1    Jun. 9, 2005

Related U.S. Application Data

(63) Continuation of application No. PCT/JP03/09017, filed on Jul. 16, 2003.

(51) Int. Cl.
*B01D 15/08* (2006.01)

(52) U.S. Cl. .............. 210/656; 210/198.2; 216/2; 216/56; 422/70; 422/100; 438/38

(58) Field of Classification Search .............. 210/656, 210/635, 198.2; 422/70, 100; 438/38; 216/2, 216/56
See application file for complete search history.

(56) References Cited

U.S. PATENT DOCUMENTS

| | | | | |
|---|---|---|---|---|
| 3,503,712 | A * | 3/1970 | Sussman ............... | 422/191 |
| 4,719,011 | A * | 1/1988 | Shalon et al. ......... | 210/198.2 |
| 4,891,120 | A | 1/1990 | Sethi et al. ........... | 204/299 R |
| 5,116,495 | A * | 5/1992 | Prohaska .............. | 210/198.2 |
| 5,165,292 | A * | 11/1992 | Prohaska .............. | 73/866 |
| 5,205,929 | A * | 4/1993 | Carr et al. ............ | 210/198.2 |
| 5,308,495 | A * | 5/1994 | Avnir et al. ........... | 210/656 |
| 5,624,875 | A | 4/1997 | Nakanishi et al. ..... | 501/39 |
| 6,136,187 | A * | 10/2000 | Zare et al. ............ | 210/198.2 |
| 6,207,098 | B1 | 3/2001 | Nakanishi et al. ..... | 264/414 |

(Continued)

FOREIGN PATENT DOCUMENTS

JP         3-56535        3/1991

(Continued)

OTHER PUBLICATIONS

C. Ericson, et al., "Electroosmosis- and Presusre-Drive Chromatography in Chips Using Continuous Beds", Analytical Chemistry, American Chemical Society, vol. 72, No. 1, pp. 81-87 (Jan. 1, 2000).

(Continued)

*Primary Examiner*—Ernest G. Therkorn
(74) *Attorney, Agent, or Firm*—Fitzpatrick, Cella, Harper & Scinto

(57) ABSTRACT

A process for producing a mass transfer device is provided which enables packing of a packing material uniformly in a flow channel, and transfers a specified substance by flowing a fluid containing the specified substance through a flow channel on a substrate. A mass transfer device produced by the process is also provided. The process for producing a mass transfer device comprises steps of preparing a substrate, forming a flow channel on the surface of the substrate, applying a liquid drop composed of a packing material and a liquid medium, and packing the packing material in the flow channel by removing the liquid medium.

9 Claims, 6 Drawing Sheets

U.S. PATENT DOCUMENTS

| | | | |
|---|---|---|---|
| 6,258,263 B1 * | 7/2001 | Henderson et al. | 210/198.2 |
| 6,264,892 B1 | 7/2001 | Kaltenbach et al. | 422/68.1 |
| 6,326,189 B1 * | 12/2001 | Fukuzono et al. | 435/287.2 |
| 6,344,120 B1 | 2/2002 | Haswell et al. | 204/450 |
| 6,444,150 B1 | 9/2002 | Arnold | 264/69 |
| 6,663,697 B1 * | 12/2003 | Kottenstette et al. | 96/101 |
| 6,673,533 B1 * | 1/2004 | Wohlstadter et al. | 435/6 |
| 6,887,384 B1 * | 5/2005 | Frechet et al. | 210/634 |
| 6,923,907 B2 * | 8/2005 | Hobbs et al. | 210/198.2 |
| 7,153,421 B2 * | 12/2006 | Koehler et al. | 210/198.2 |
| 7,217,359 B2 * | 5/2007 | Nakanishi et al. | 210/198.2 |
| 2002/0182627 A1 * | 12/2002 | Wang et al. | 435/6 |
| 2002/0187557 A1 * | 12/2002 | Hobbs et al. | 436/161 |
| 2003/0159993 A1 * | 8/2003 | Yin et al. | 210/656 |
| 2003/0217923 A1 * | 11/2003 | Harrison et al. | 204/450 |
| 2003/0230524 A1 * | 12/2003 | Soga et al. | 210/198.2 |
| 2005/0006293 A1 * | 1/2005 | Koehler et al. | 210/198.2 |

FOREIGN PATENT DOCUMENTS

| | | | |
|---|---|---|---|
| JP | 3-212451 | | 9/1991 |
| JP | 9-329590 | | 12/1997 |
| JP | 11-133014 | | 5/1999 |
| JP | 2002-218629 | | 8/2002 |
| JP | 2002-311008 | | 10/2002 |
| WO | WO 01/38865 | * | 5/2001 |
| WO | WO 01/53819 | | 7/2001 |
| WO | WO 01/85602 | | 11/2001 |
| WO | WO 02/101383 | | 12/2002 |

OTHER PUBLICATIONS

Database WPI, XP002256826, Section Ch, Week 199214, Derwent Publications Ltd. (Jun. 30, 1991).

* cited by examiner

PROCESS FOR PRODUCING MASS TRANSFER DEVICE AND APPARATUS FOR PRODUCTION THEREOF

This is a continuation of International Application PCT/JP2003/09017, filed Jul. 16, 2003.

TECHNICAL FIELD

The present invention relates to a process for producing a mass transfer device for transferring a substance in a fluid, and relates also to an apparatus for producing the device.

BACKGROUND ART

Various types of chromatography, so-called preparatory chromatography, are employed as a means for isolating a pure substance from a mixture or separating a mixture. Of the chromatography, widely utilized is liquid chromatography, particularly high-performance liquid chromatography (HPLC).

Pure substances are different in the molecular size, molecular shape, electric charge, viscosity, mobility, and polarity, and are greatly different in the extent of the interaction with a packed material of chromatography, resulting in difference of migration rates in the chromatography. By utilizing the difference of the migration rate, a mixture can be separated into its components. From the viewpoint of transfer of a pure substance by the principle of the separation, the chromatography apparatus including the HLPC is regarded as a mass transfer device.

The HLPC employs widely a capillary column packed with a particulate packing material. The particulate packing material includes particulate porous silica gel, surface-modified particulate silica gel, and particulate polymer gel, having a particle size of about 5 to about 10 $\mu$m.

On the other hand, with development of microfabrication techniques in recent years, the systems are attracting attention which comprise a fine flow channel, microfluidic devices such as a pump, and a valve, and a sensor integrated on a substrate like glass or silicon, and which conduct chemical analysis on the substrate. Such a system is called a microanalysis system, a $\mu$-TAS (Micro Total Analysis System), or a Lab on a Chip. The miniaturization of the chemical analysis system enables decrease of a noneffective space volume and remarkable decrease of the sample size as well as shortening of the analysis time and decrease of power consumption of the entire system. Further, the miniaturization is promising for lowering the price of the system. Furthermore, the U-TAS is promising in medical services such as home medial care and bed-side monitoring, and biological chemical techniques such as genomics and proteomics analysis.

HLPC is promising for increasing the performance and lowering the cost by miniaturizing the system to form a fine flow path packed with a packing material. However, a conventional particulate packing material cannot readily be packed uniformly into a fine flow channel owing to the shape and size of the particles.

Japanese Patent Application Laid-Open Nos. 9-329590 and 11-133014 disclose columns employing a silica gel of a double pore structure without using a particulate packing material. The columns are prepared by treating a silica gel chemically and thermally in a tubular mold of inside diameter of 10 mm, and after the molding, the surrounding surface is solidified by an epoxy resin in a form of a rod column. However, the column prepared by the above method has a diameter of 10 mm and a length of about 83 mm. Therefore, the column is not useful for $\mu$-TAS.

Japanese Patent Application Laid-Open No. 2000-218629 discloses a process for injection-molding a $\mu$-TAS chip having a groove as a flow channel. However, this $\mu$-TAS chip is not packed with a packing material, so that it is not useful for HPLC.

U.S. Pat. No. 6,344,120 discloses a process for forming a porous silica structure in a flow channel by forming a microscopic channel path on a surface of a plate, introducing a solution in a sol state into the flow channel, and allowing the solution to gel in the flow channel.

DISCLOSURE OF THE INVENTION

The present invention intends to provide a process for producing a mass transfer device which is capable of holding a packing material uniformly in a flow channel having a cross-section size ranging from several ten $\mu$m to several hundred $\mu$m. The present invention intends also to provide a mass transfer device which is as small as several cm×several cm, yet have high performance and can be produced at a low cost.

According to an aspect of the present invention, there is provided a process for producing a mass transfer device for transferring a specified substance by flowing a fluid containing the specified substance through a flow channel on a substrate, comprising the steps of (a) preparing a substrate (hereinafter also a "substrate preparing step"),
(b) forming a flow channel on the surface of the substrate (hereinafter also a "flow channel forming step"),
(c) applying drops of a liquid comprised of a packing material and a liquid medium into the flow channel (hereinafter also a "packing material applying step"), and
(d) packing the packing material in the flow channel by removing the liquid medium (hereinafter also "a liquid medium removing step"), wherein the drops of the liquid are applied in a number of drops necessary to fill the packing material into the flow channel, and the packing material exerts action on the specified substance in the fluid flowing through the flow channel packed with the packing material.

According to another aspect of the present invention, there is provided an apparatus for producing the mass transfer device for transferring a specified substance by flowing a fluid containing the specified substance through a flow channel on a substrate, comprising a means for applying drops of a liquid comprised of a packing material and a liquid medium into the flow channel (hereinafter also a "liquid drop applying means"),
a means for driving the liquid drop applying means, and
a means for removing the liquid medium to pack the packing material in the flow channel,
wherein the drops of the liquid are applied in a number of drops necessary to fill the packing material into the flow channel by removal of the liquid medium, and the packing material packed in the flow channel exerts action on the specified substance in the fluid flowing through the flow channel.

DESCRIPTION OF THE PREFERRED EMBODIMENTS

The present invention is described below in detail.

Figure 1A:
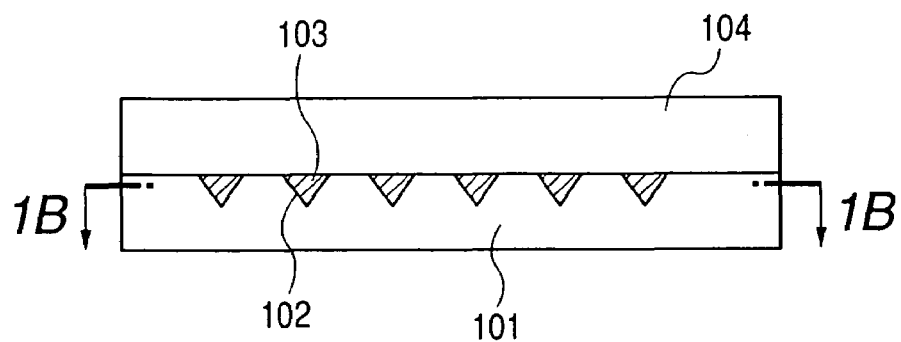
FIGS. 1A and 1B illustrate schematically an example of a mass transfer device prepared by the production process of the present invention.
Figure 1B:
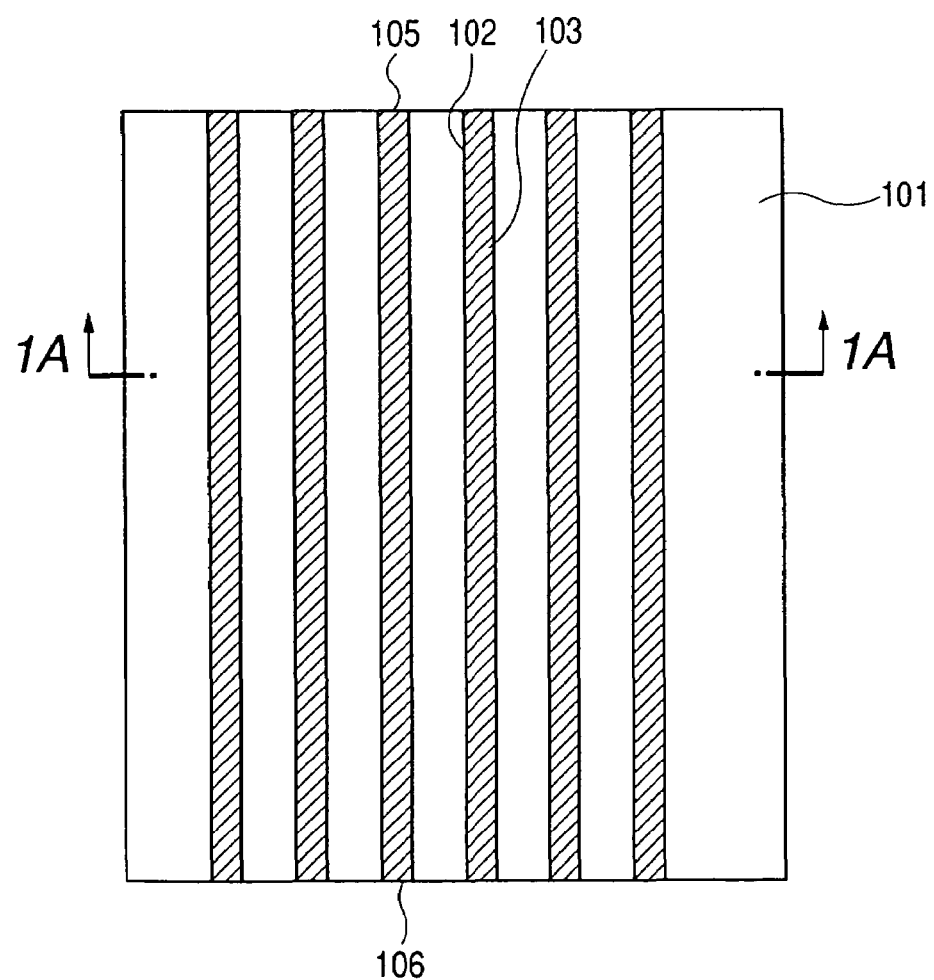

FIGS. 1A and 1B illustrate schematically an example of a mass transfer device prepared by the production process of the present invention. FIG. 1A is a vertical sectional view taken along line 1A-1A in FIG. 1B. FIG. 1B is a horizontal sectional view taken along line 1B-1B in FIG. 1A.

The mass transfer device of the present invention has flow channels 102 formed on substrate 101. Flow channel 102 is packed with packing material 103. Packing material 103 is intercepted by intercepting member 104 from the outside air. At the both ends of the flow channel, are provided inlet 105 for introducing a fluid (hereinafter also a "fluid sample" or a "sample solution") containing a specific substance (hereinafter also a "specified substance" or a "transfer object substance") to be separated in the fluid, and outlet 106 for discharging the fluid having passed through the flow channel.

The planar shape of the flow channel is not specially limited. For example, straight flow channels may be arranged in a large number on a substrate to allow a large number of fluid samples to flow concurrently to enable effective transfer of the transfer objective substance for analysis. A spiral or snaky flow channel can give a longer flow channel to increase the performance in separating the transfer object substances per unit area of the substrate.

The shape of the cross section of the flow channel cut perpendicularly to the fluid flow direction (hereinafter also a "flow channel cross-section"), which is shown in vertical sectional view, is not specially limited, including a V shape as shown in FIG. 1, a semicircle shape, a semiellipsoid shape, and a quadrangle shape. The dimension of the flow channel cross-section is preferably in the range from several ten μm to several hundred μm in depth and in breadth.

The inlet and the outlet may be formed at the end faces of the substrate, or formed on the substrate constituting the bottom or side wall of the flow channel, or intercepting member constituting the top cover of the underlying flow channel.

The fluid sample introduced from inlet 105 is allowed to migrate through flow channel 102. The fluid sample may be gaseous or liquid.

The packing material is preferably selected from those which causes difference in the migration rate between the transfer object substances, or causes a chemical reaction of a transfer object substance. In other words, the action of the packing material on the transfer object substances means action of causing difference in the migration rate between the migration object substances in the fluid sample to make them separate from each other, action of causing chemical reaction of the transfer object substance, and like actions.

The type or activity of the interaction of the packing material with a transfer object substrate can be varied by preliminary surface treatment of the packing material with a coupling agent or the like. The respective transfer object substances having passed through the flow channel are discharged separately from the outlet owing to the difference in the migration rate. The discharged transfer object substance is detected by a detector to identify the transfer object substance.

The mass transfer device of the present invention is useful also as a "micro-reactor" for causing a chemical reaction of the substance introduced into the packing material. For this purpose, a substance which is chemically reactive to the fluid sample or the transfer object substance is employed as the packing material, or a substance which is chemically active or can catalyze a chemical reaction is kept on the packing material. A packing material comprised of a porous material can increase the reaction efficiency owing to the larger reaction surface area.

The process for producing the mass transfer device of the present invention is explained by reference to FIGS. 2A to 2G which are sectional views taken along line 1A-1A in FIG. 1B.

Figure 2A:
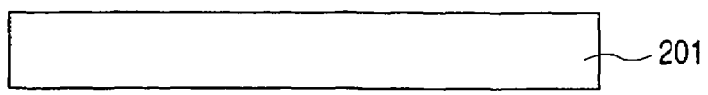
FIGS. 2A, 2B, 2C, 2D, 2E, 2F, and 2G are flow charts showing an example of the process of producing the mass transfer device of the present invention.

Firstly, substrate 201 is prepared as shown in FIG. 2A. The material of substrate 201 is not specially limited, provided that the material is resistant against the fluid sample, including semiconductors such as silicon; glass; metals such as stainless steel; and resins such as PDMS (polydimethylsiloxane), PMMA (polymethyl methacrylate), and PS (polystyrene).

Figure 2B:
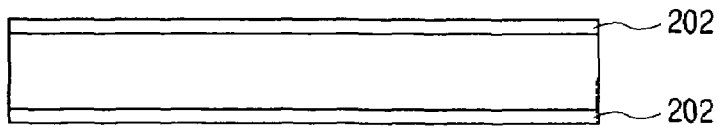
Figure 2C:
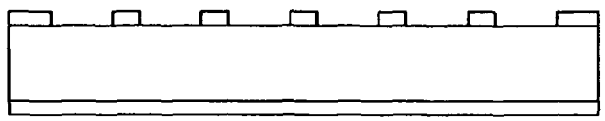
Figure 2D:
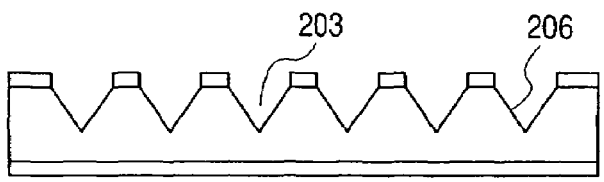

Next, the main portion of the wall is formed for constituting the flow channel, excluding the portion of the intercepting member described later. The flow channel may be formed by a method such as etching of the substrate, and formation of a partition wall on the substrate. Any desired shape of the flow channel can be formed on the substrate by etching the substrate by use of an etching mask prepared by photolithography. In particular, a substrate, which is made of monocrystalline silicon, can be etched to form the flow channel with high precision by anisotropic crystal etching. Otherwise, any desired shape of the flow channel can be formed by forming a partition wall constituted of a thick resist film on the substrate by photolithography. In FIGS. 2B to 2D, substrate 201 composed of a monocrystalline silicon plate is thermally oxidized to form thermal oxidation film 202 composed of $SiO_2$ on both faces of monocrystalline silicon substrate 201 (FIG. 2B); thermal oxidation film 202 is patterned by etching to bare the silicon of the substrate face at the portion corresponding to the prescribed flow channel (FIG. 2C); and the silicon crystal is etched anisotropically by utilizing patterned thermal oxidation film 202 as the etching mask to form flow channel 203 in a groove shape on monocrystalline silicon substrate 201 (FIG., 2D).

Figure 2E:
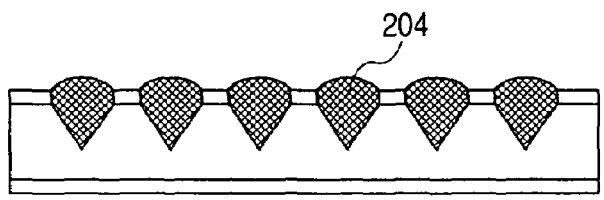

Then, packing material 204 is filled in flow channel 203 as shown in FIG. 2E. In the production process of the present invention, after the step of formation of the flow channel wall on the substrate, the flow channel is open upward as shown in FIG. 2D, and the packing material is filled from the open side into the flow channel. Therefore, the packing material can readily be filled in comparison with filling into a tube or the like in the direction perpendicular to the cross section of the flow channel.

In the production process of the present invention, the packing material is filled into the flow channel by applying a drop of a liquid (hereinafter also a "packing material liquid") comprised of the packing material and the liquid medium by a certain liquid application method. The liquid application method includes dispenser methods, inkjet methods, spin coating methods, dip coating methods, roll coating method, bar coating methods, and spray coating methods. For filling a predetermined amount of the packing material into the flow channel, the drop of the packing material liquid should be applied in a precise amount in a predetermined number of the drops. Therefore, a dispenser method or an inkjet method is preferred which is capable of applying a precise amount of the liquid drop.

The dispenser system and the inkjet system are both capable of applying a liquid by energizing a fluid. The methods of liquid application by the dispenser system include air methods, tubing methods, gear methods, piston methods, and screw methods. The type of liquid application by the inkjet system includes thermal methods (utilizing thermal expansion of a bubble), piezo methods employing a piezo element, and electrostatic methods. A suitable method is selected depending on the kind and amount of the packing material. The inkjet method can apply a precise amount of the packing material liquid effectively by ejection of liquid droplets by an inkjet head to an intended position in the flow channel of an arbitrary shape, even if the breadth of the flow channel is as small as about 10 μm.

The inkjet system can eject a liquid drop of a volume of as small as several pL. The number of the ejected liquid drops can be controlled by controlling the number of the pulse voltage applied to the inkjet head.

Figure 2F:
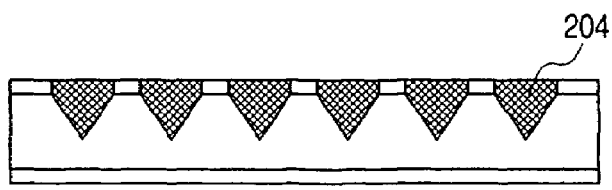

The predetermined amount of the packing material liquid means the amount of the liquid for obtaining a state of the packing material, after removal of the liquid medium, slightly rising from the surface of the substrate as shown FIG. 2E, or obtaining a state of the packing material having the surface on a common level as the substrate surface as shown in FIG. 2F. If the surface of the packing material after removal of the liquid medium is concave from the surface of the substrate, a portion of the liquid sample introduced into the flow channel for transfer of the transfer object substance may flow along the concave without receiving the action of the packing material undesirably. The rising portion of the packing material is worked to level the surface of the substrate and the surface of the packing material.

As explained above, the dispenser method and the inkjet method, which are capable of applying a precise amount of the liquid drop in a prescribed number of drops of the packing material liquid into the flow channel, enable significant decrease of the amount of the packing material necessary for filling, and reduction of the filling cost.

The packing material after the step (d) of the present invention contains preferably a porous material. By making the packing material porous in the final state, exploring and election of any particulate packing material capable of providing in a packed state the same porosity as that by the porous material are unnecessary for obtaining the porosity. Moreover, by controlling the pore size and pore size distribution of the porous material, the mass transfer device can be produced to meet various application fields. An example of the porous material is porous silicon dioxide.

One method for making porous the packing material in the final state is a so-called sol-gel method in which the packing material in a sol state is packed into a flow channel and then allowed to gel in the flow channel. The sol-gel method will be explained later in detail.

In the next step, for packing the packing material without an empty space in the flow channel, the surface of the substrate and the top face of the packing material are brought to a common level as shown in FIG. 2F. This step can be conducted by polishing or etching-back.

Various mass transfer devices can be produced for various application fields by treating the surface of the packing material as necessary, for example, to control the hydrophobicity or hydrophilicity of the surface. In the production process of the present invention, the flow channel packed with the packing material is open on the face parallel to the fluid flow direction. Therefore, the surface of the packing material can be readily treated in comparison with treatment of a packing material packed in a closed flow channel such as a tube.

The method for surface treatment of the packing material includes immersion of the packing material together with the substrate into a surface-treating agent solution (dip-coating), and dropping of a surface treating agent solution into the packing material by a dispenser or an inkjet head. In particular, by using an inkjet head, the packing material portion is selectively and efficiently surface-treated even if the fine flow channel has a breadth of as small as several ten μm.

Figure 2G:
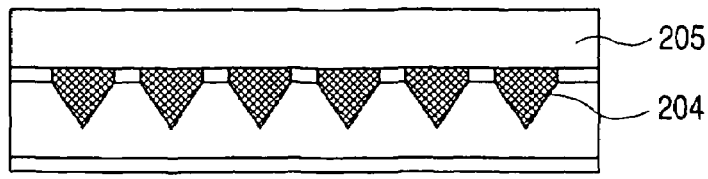

In the next step, the packing material is intercepted from the outside air by an intercepting member as shown in FIG. 2G.

The material of the intercepting member is not specially limited, provided that the material is resistant to the fluid sample. The material may be the same as or different from that of the substrate. The intercepting member is bonded to the substrate by a suitable method selected depending on the combination of the materials of the substrate and the intercepting member. For example, anodic bonding is employed for combination of silicon-glass; and heat fusion bonding or chemical fusion bonding by HF (hydrofluoric acid) is suitable for combination of glass-glass. An adhesive like an epoxy adhesive is also effective for the bonding.

In the production process of the present invention, a sol-gel method is preferably employed in which the packing material in a sol state is filled into a flow channel and then allowed to gel in the flow channel. The sol-gel method is a material synthesizing process in which a source material in a fluidic solution state (sol) is converted to a solid (gel) by physical or chemical change of the constituting component. In particular, for inorganic materials such as glass and ceramics, the sol-gel method is called a low-temperature synthesis method in comparison with the fusion-sintering process at a high temperature. This process is applicable to a material in a shape of fine particles, fibers, thin films, and so forth with high freedom in selection of the material. This process is attracting attention in recent years as the technique for preparing organic-inorganic hybrids, namely complexes of an organic component with an inorganic component in a molecular level. Various organic-inorganic complexes of such a structure are reported which are obtained by blending uniformly an organic polymer and an inorganic substance. Uniform transparent organic-inorganic complex are prepared from an organic polymer and an inorganic substance. For example, Japanese Patent Application Laid-Open No. 3-56535 and 3-212451 disclose a technique for producing a complex. In this process, a hydrolysis-polymerizable inorganic compound like tetraalkoxysilane is hydrolysis-polymerized in the presence of an organic polymer containing an amide linkage like polyoxazoline to obtain an inorganic oxide gel like silica gel. The resulting complex contains an amide linkage-containing non-reactive polymer like an oxazoline polymer dispersed uniformly in a three-dimensional fine network structure (matrix).

In the original type of the sol-gel process employed in the present invention, a solution is allowed to gel by molding into an intended shape, and the liquid medium is removed by heating to change the gel to a glassy or ceramic material. For example, a solution of an alkoxide of a metal such as silicon, boron, titanium, and aluminum, or of an organic or inorganic compound is treated for hydrolysis-polymerization to form a sol containing a fine particulate reaction product of a metal hydroxide or the like, and further treated for reaction to form a gel. The resulting porous gel is heated to obtain a non-crystalline, glassy, or polycrystalline material. Silicon dioxide employed as the source material is allowed to react usually at a temperature ranging from a room temperature to 80° C. and the product is dried at a temperature of 40 to 120° C.

An example of the sol-gel method is described below more specifically.

A metal alkoxide is selected for the intended oxide, and an alcohol is selected as the solvent. They are mixed into a solution. Water, as a hydrolysis reagent for the alkoxide, and an acid, as a catalyst are added to the solution thereof. The acid serves also to prevent precipitate formation and liquid phase separation to give uniform solution. As the catalyst, an acid such as hydrochloric acid, sulfuric acid, nitric acid, and acetic acid is used, and ammonia may be used. In some case, An additive such as acetylacetone and formamide may be used if necessary.

In the present invention, any material other than those described above may be useful depending on the transfer object substance, provided that the packing material liquid thereof is an a sol state in the packing material liquid-applying step (c) and can become a gel by treatment after the packing operation. A particularly suitable material and a process for production thereof are disclosed in U.S. Pat. No. 5,624,875 and U.S. Pat. No. 6,207,098. The material and the principle and feature of the production process are described below.

Silicon alkoxide is allowed to react with water in the presence of a polymer to form silica. The formed silica polymerizes and flocculates. Then the solution separates into the phases of the silica and the other portion, and concurrently the silica in a liquid sol transforms into a solid gel. The liquid portion is removed, and the polymer is removed by heat treatment to obtain porous silica gel. This gel has many voids of 500 nm or larger in the interior of the gel. The voids are traces of the solvent phase remaining in the silica by retaining the continuous structure owing to the sol-gel transformation during the phase separation. Such voids distribute in a network in the interior of the gel, and finer voids (5 to 100 nm, usually about 10 nm) are contained in the silica skeleton, forming a stratum structure. The voids in the skeleton are controllable by changing the amount and kind of the polymer added.

EXAMPLES

The present invention is explained below in more detail by reference to Examples.

Example 1

A mass transfer device shown in FIGS. 1A and 1B was produced in this Example. A single crystalline silicon substrate 101 (40 mm×40 mm, 0.625 mm-thick) was used as the substrate. This device had flow channels 102 having a cross-section of V-shaped grooves on substrate 101, and flow channels 102 were packed with porous silicon dioxide as a packing material to form columns 103. The surfaces of the packing material were treated for hydrophilicity with octadecyldimethylchlorosilane (not shown in the drawing). Columns 103 were intercepted from the outside air by intercepting member 104 comprised of a monocrystalline silicon substrate. Inlets 105 were provided for introducing a fluid into flow channels 102 at one end face of monocrystalline silicon substrate 101, and outlets 106 were provided for discharging the fluid having passed through flow channels 102 at the end face opposite to the face having inlet 105.

The process for producing the mass transfer device of this Example is explained by reference to FIGS. 2A to 2G.

Firstly, monocrystalline silicon substrate 201 having a face of Miller index (100) was prepared (FIG. 2A).

Substrate 201 was thermally oxidized to form thermal oxidation films 202 of $SiO_2$ 5000 Å in thickness on the both faces of substrate 201 (FIG. 2B). Thermal oxidation film 202 was utilized later as an etching mask.

Thermal oxidation film (202) was patterned by photolithography and with an aqueous HF solution to bare the silicon substrate at the portions corresponding to the intended flow channels (FIG. 2C).

Substrate 201 was etched anisotropically by an aqueous 22 wt % TMAH (tetremethylammonium hydroxide) solution at a solution temperature of 88° C. by use of a patterned thermal oxidation film (202) as the etching mask to form a groove-shaped flow channel 203 constituted of a wall 206 consisting of crystal plane (111) (FIG. 2D). The cross section of the flow channel had a size of about 100 μm in breadth and about 70 μm in depth.

Separately, zirconium n-butoxide (NBZ) was added to a mixture formed of a tetraethoxysilane solution in ethanol and a hydrochloric acidic ethanol solution, and the mixture was allowed to react for one hour to obtain a reaction solution. This reaction solution was added to an aqueous ammoniacal ethanol solution to form a packing material liquid. The packing material liquid was applied to flow channels 203 by an inkjet head from above the substrate 201 in an amount sufficient to fill flow channels 203.

The substrate having the applied packing material liquid applied thereon was kept at room temperature for two hours for gelation of the packing material liquid. The gel was dried at 40° C. for two hours, and was heat-treated at 200° C. for two hours to form flow channels 204 packed with porous silicon dioxide (hereinafter also "a column" or "columns") on monocrystalline silicon substrate 201 (FIG. 2E).

The portions of columns 204 rising from the upper face of substrate 201 were polished to level the surface of the columns and the upper face of substrate 201 (FIG. 2F).

To polished columns 204, a solution of octadecyldimethylchlorosilane was dropped by an inkjet head for coupling treatment of the surface of the porous silicon dioxide constituting the column. This treatment makes the porous silicon dioxide to be useful as a packing material of reversed phase system (ODS system).

Then onto the upper face of substrate 201, another monocrystalline silicon substrate 205 as an intercepting member was bonded by an epoxy adhesive to intercept columns 204 from the outside air (FIG. 2G).

The both ends were cut by dicing perpendicularly to the direction of the flow of the fluid through flow channels 203 to form inlets (not shown in the drawing) and outlets (not shown in the drawing). Thus the mass transfer device as shown in FIGS. 1A and 1B was completed.

From inlet 105 of the mass transfer device of this Example, a solution of a mixture of polyethylene glycol (molecular weight 1000) and tetraethylene glycol (molecular weight 242) was introduced. A capillary (not shown in the drawing) was connected thereto and connected further to a pump (not shown in the drawing). The mixture solution was sent into flow channel 102 by applying a pressure to inlet 105 by the pump. The mixture solution was allowed to pass through flow channel 102 under separation action of porous silicon dioxide 204 and reached outlet 106. Outlet 106 is connected to a capillary (not shown in the drawing), and the solution was delivered from outlet 106 through the capillary to a differential refractometer (not shown in the drawing) to measure the refractive index.

As the results of the refractive index measurement, distinct two peaks of the output signal were obtained owing to the elution time difference between polyethylene glycol and tetraethylene glycol.

According to this Example, plural flow channels can be formed simultaneously on one substrate by employing a three-dimensional fine processing technique for semiconductors. The produced mass transfer device has plural flow channels as shown in FIGS. 1A and 1B. Thereby, different substances can be concurrently analyzed, and analysis efficiency is improved and the analysis cost is reduced.

In this Example, the flow channels were formed by anisotropic etching of a silicon crystal with a high working precision. Although a monocrystalline silicon (100) was used as the substrate in this Example, groove-shaped flow channels constituted of {111} plane can be formed on a (100) monocrystalline silicon substrate by anisotropic etching of the crystal.

Example 2

Figure 3A:
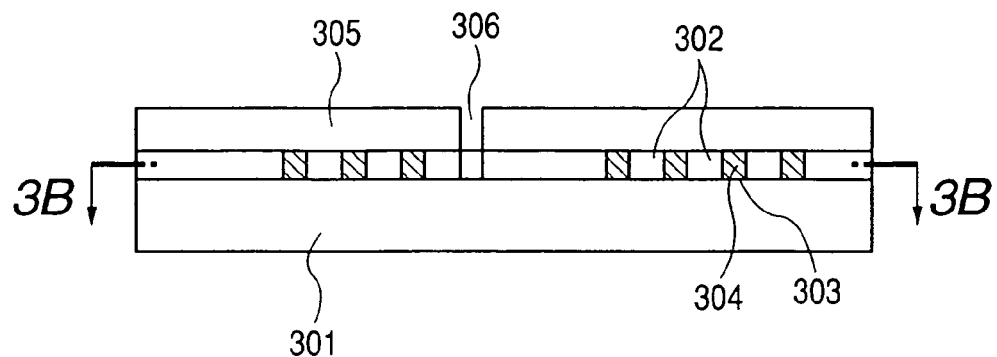
FIGS. 3A and 3B illustrate schematically another example of a mass transfer device prepared by the production process of the present invention.
Figure 3B:
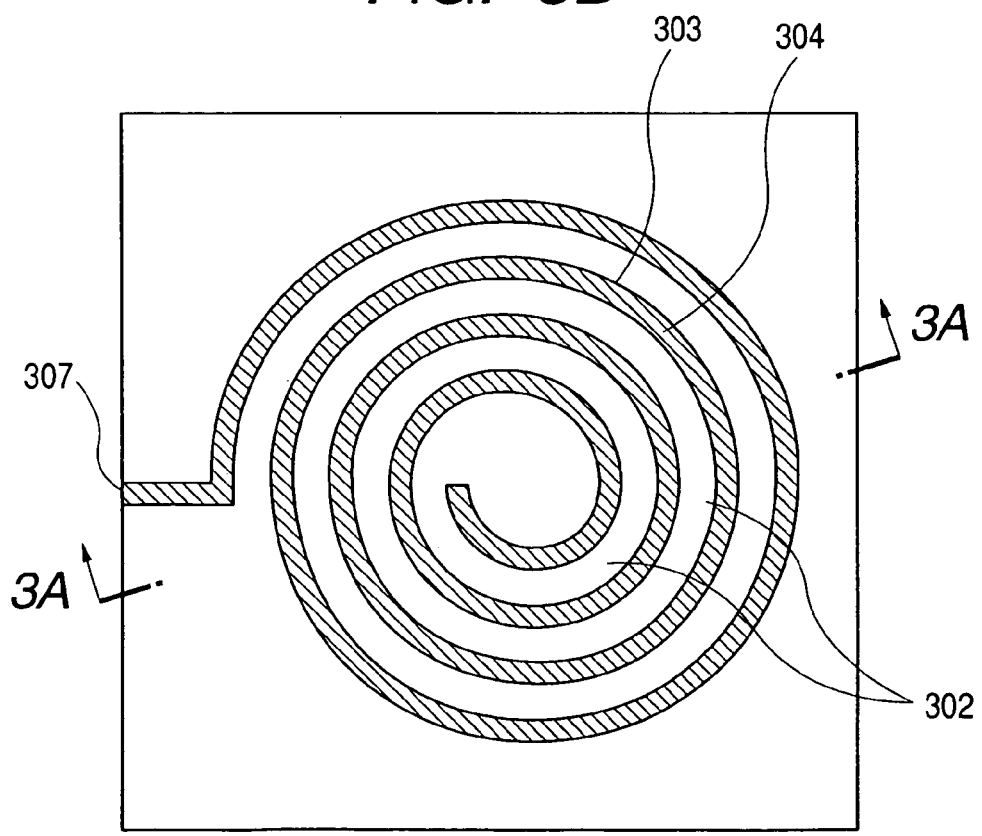

A mass transfer device as shown in FIGS. 3A and 3B was produced in this Example.

Monocrystalline silicon substrate 301 was used as the substrate for the mass transfer device in this Example. On monocrystalline silicon substrate 301, a spiral flow channel 303 was provided by forming a partition wall 302. Porous silicon dioxide was packed as the packing material in flow channel 303 to constitute column 304. The surface of the porous silicon dioxide was treated with octadecyldimethylchlorosilane (not shown in the drawing). Column 304 was intercepted from the outside air by an intercepting member constituted of glass substrate 305. Inlet 306 was provided to penetrate through intercepting member 305 for introducing a fluid into flow channel 303. The fluid introduced from inlet 306 was allowed to flow through flow channel 303 and was discharged from outlet 307 formed on the end face of the mass transfer device.

The process for producing the mass transfer device of this Example is explained by reference to FIGS. 4A to 4G viewed in the direction of cross section along line 3A-3A in FIG. 3B.

Figure 4A:
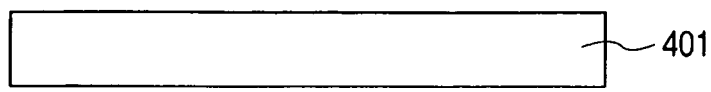
FIGS. 4A, 4B, 4C, 4D, 4E, 4F, and 4G are flow charts showing another example of the process of producing the mass transfer device of the present invention.

Monocrystalline substrate 401 was used as the substrate (FIG. 4A).

Figure 4B:
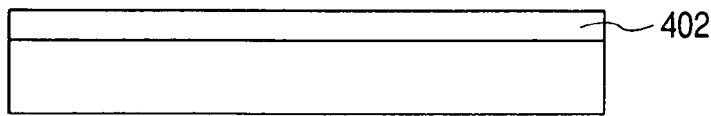

Substrate 401 was coated with thick-film resist 402 (trade name: SU-8, Micro Chemical Corp.) in a film thickness of 100 μm by spin coating (FIG. 4B).

Figure 4C:
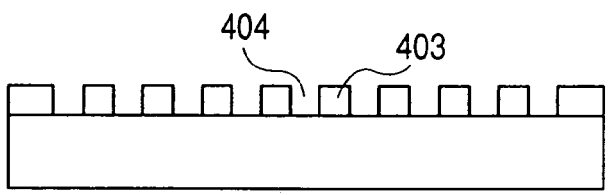

Thick-film resist 402 was patterned in a spiral shape as shown in FIG. 3B by photolithography to form partition wall 403 and flow channel 404 (FIG. 4C).

Separately, zirconium n-butoxide (NBZ) was added to a mixture of a tetraethoxysilane solution in ethanol and a hydrochloric acidic ethanol solution, and the mixture was allowed to react for one hour to obtain a reaction solution. This reaction solution was filled dropwise to flow channel 404 by an inkjet head. Further thereto, an aqueous ammoniacal ethanol solution was added dropwise into the flow channel by an ink jet head. The above reaction solution was added dropwise in an amount sufficient to fill flow channel 404.

Figure 4D:
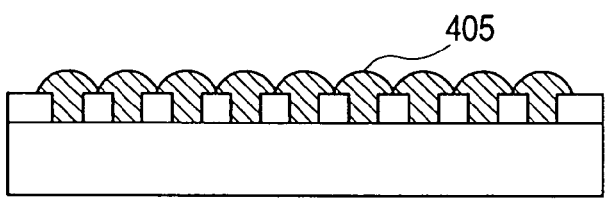

The substrate having the packing material liquid applied thereon was kept at room temperature for two hours for gelation of the packing material liquid. The gel was dried at 40° C. for two hours, and was heat-treated at 200° C. for two hours. Thereby, column 405 composed of porous silicon dioxide was formed in flow channel 404 (FIG. 4D).

Figure 4E:
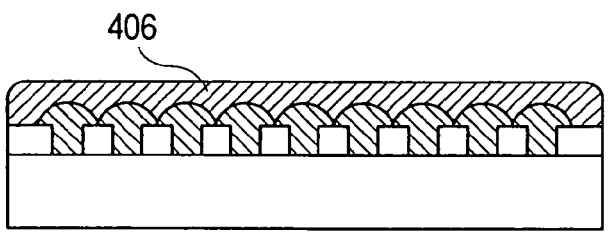

Then, silicone resin 406 was applied on the upper face of the substrate by spin coating, and heat-treated for flattening of the surface by reflowing (FIG. 4E).

Figure 4F:
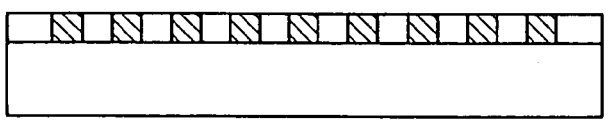

Silicone resin 406 and column 405 on the upper face of the substrate were dry-etched by use of a gas mixture containing $CF_4$ gas and $O_2$ gas. In the dry etching, the etching rate of silicone resin 406 and that of column 405 were adjusted to be equal by controlling the gas ratio and the gas pressure. In this state, the etching was conducted until the upper face of column 405 and the upper face of partitioning wall 403 became leveled by so-called etching-back (FIG. 4F).

Octadecyldimethylchlorosilane (not shown in the drawing) was dropped by an inkjet head to flow channel 404 for coupling treatment of the surface of the porous silicon dioxide 405. This treatment makes the porous silicon dioxide useful as a packing material of reversed phase system (ODS system).

Figure 4G:
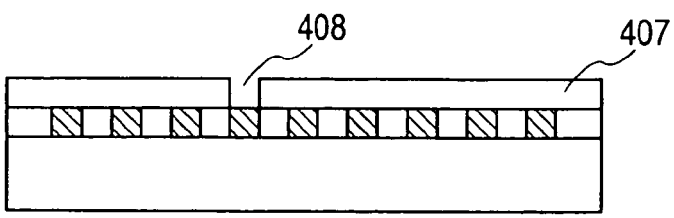

Then onto the upper face of substrate 401, another monocrystalline silicon substrate 407 as an intercepting member was bonded by an epoxy adhesive to intercept column 405 from the outside air. Inlet 408 was formed preliminarily through glass substrate 407 at the position corresponding to the starting point of flow channel 404 (FIG. 4G).

Through the above process, the mass transfer device shown in FIGS. 3A and 3B was completed.

The mass transfer device shown in FIGS. 3A and 3B was employed for separation of proteins.

A sample solution was prepared which contained four kinds of proteins, ribonuclease, cytochrome C, lactoalbumin, and mioglobulin respectively at a final concentration of 0.5% (w/v) in a $14 \times 10^{-3}$ mol/L trishydroxymethylaminomethane-hydrochloric acid buffer solution (pH 8.1). This sample solution was introduced from inlet 306. A capillary (not shown in the drawing) was connected thereto and the capillary was connected further to a pump (not shown in the drawing). The mixture solution was sent into flow channel 303 by applying a pressure to inlet 306 by the pump. Further, as the mobile solvent, acetonitrile-water (50/50 (v/v) containing 0.1% trifluoroacetic acid was fed continuously from the pump. The proteins in the sample solution were separated during passage through flow channel 303 by action of porous silicon dioxide 304 modified for ODS, and reached successively the outlet 307.

Outlet 307 was connected to a capillary (not shown in the drawing), and the solution was delivered from outlet 307 through the capillary to a UV-visible light spectrometer (220 nm) (not shown in the drawing) to detect the proteins. As the results of the detection, the proteins were separated effectively, and were found to have reached the outlet in the order of ribonuclease, cytochrome C, lactoalbumin, and mioglobulin.

In this Example, the flow channel was formed by forming the partition wall by photolithography. Thereby, the flow channel can be formed in a desired shape other than the linear shape. In the mass transfer device of this Example, the flow channel was formed in a spiral shape to make the flow channel longer in comparison with a linear flow channel. In such a manner, the substance separation performance of HPLC can be improved.

Example 3

Figure 5A:
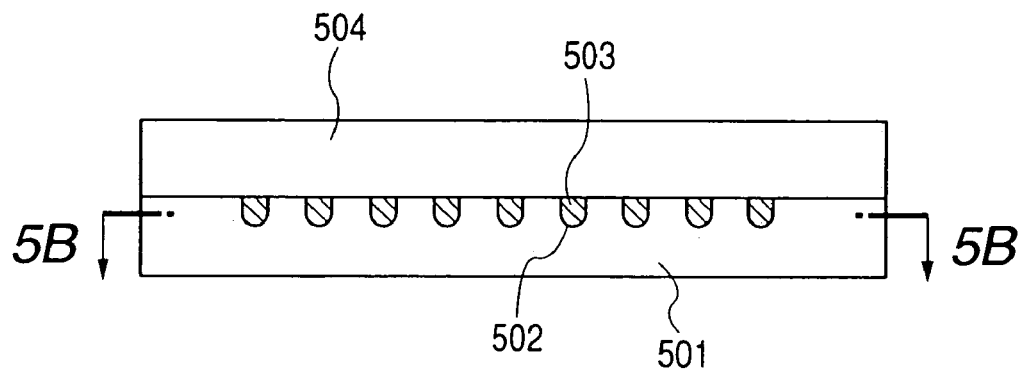
FIGS. 5A and 5B illustrate schematically still another example of a mass transfer device prepared by the production process of the present invention.
Figure 5B:
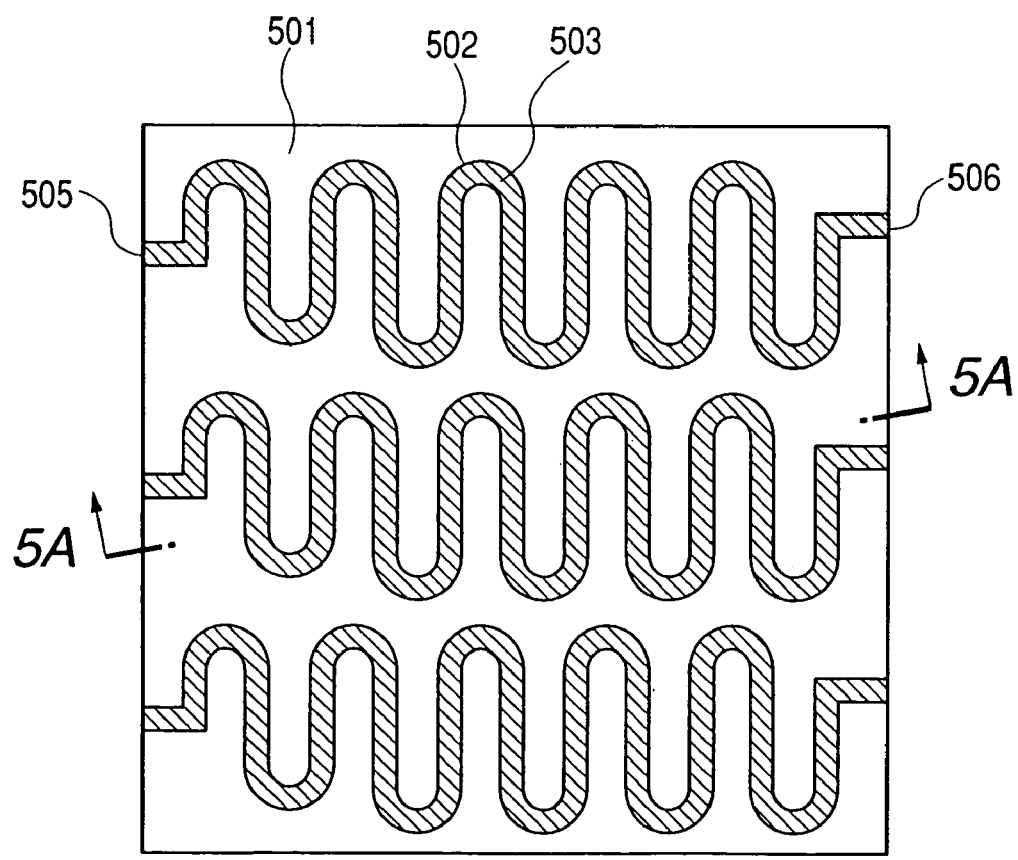

A mass transfer device as shown in FIGS. 5A and 5B was produced in this Example.

Glass substrate 501 was used as the substrate for the mass transfer device in this Example. On glass substrate 501, snaky flow channels 502 were provided by forming grooves. Porous silicon dioxide was packed as the packing material in flow channels 502 to constitute columns 503. The surface of the porous silicon dioxide was treated with octadecyldimethylchlorosilane (not shown in the drawing). Columns 503 were intercepted from the outside air by an intercepting member constituted of glass substrate 504. Inlets 505 were provided for introducing a fluid into flow channels 502 at one end face of glass substrate 501, and outlets 506 were provided for discharging the fluid having passed through flow channels 502 at the end face opposite to the face having inlet 505.

The process for producing the mass transfer device of this Example is explained by reference to FIGS. 6A to 6F viewed in the direction of cross section along line 5A-5A in FIG. 5B.

Figure 6A:
FIGS. 6A, 6B, 6C, 6D, 6E and 6F are flow charts showing still another example of the process of producing the mass transfer device of the present invention.

Glass substrate 601 was used as the substrate (FIG. 6A).

Chromium (Cr) film 602 was formed in a thickness of 1.8 μm on glass substrate 601 by sputtering.

Figure 6B:
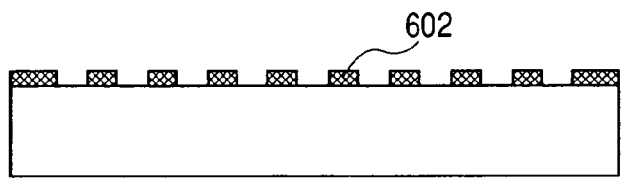

Cr film 602 was patterned by lithography and by use of an aqueous solution of a mixture of $(NH_4)_2[Ce(NO_3)_6]$ and $HClO_4$ in a shape of the snaky flow channels as shown in FIG. 5 (FIG. 6B).

Figure 6C:
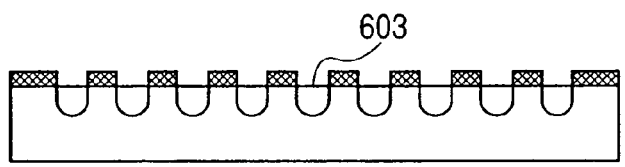

Then glass substrate 601 was etched by high-density plasma utilizing a gas mixture of $C_4F_8$ gas and Ar gas and by utilizing the above patterned Cr film 602 as an etching mask to form flow channel 603 (FIG. 6C).

Figure 6D:
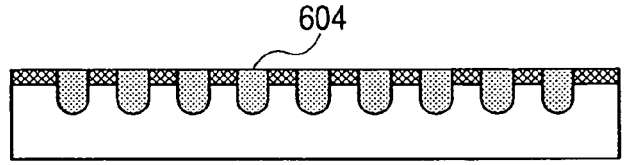

Separately, zirconium n-butoxide (NBZ) was added to a mixture of a tetraethoxysilane solution in ethanol and a hydrochloric acidic ethanol solution, and the mixture was allowed to react for one hour. The resulting solution mixture was added to an aqueous ammoniacal ethanol solution to obtain a reaction solution. This reaction solution was added dropwise to flow channels 603 by an inkjet head. The substrate having the packing material liquid applied thereon was allowed to react at room temperature for two hours for gelation of the packing material liquid. The gel was dried at 40° C. for two hours, and was heat-treated at 200° C. for two hours. By the above process, porous silicon oxide was packed in the flow channel to form columns 604 (FIG. 6D).

Figure 6E:
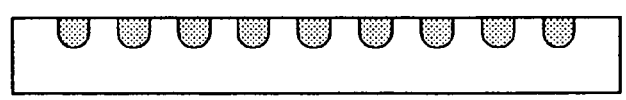

Cr film 602, glass substrate 601, and columns 604 on the upper face of the substrate were polished to make the face of glass substrate 601 and porous column 604 to have a common flat face (FIG. 6E).

An octadecyldimethylchlorosilane solution was dropped by an inkjet head to onto the packing material constituting column 604 for coupling treatment of the surface of the porous silicon dioxide. This treatment makes the porous silicon dioxide to be useful as a packing material for reversed phase system (ODS system).

Figure 6F:
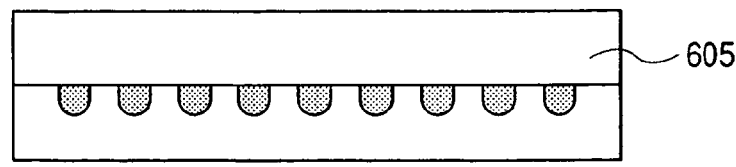

Then onto the upper face of substrate 601, another glass substrate 605 as an intercepting member was bonded by an epoxy adhesive to intercept column 604 in the flow channel from the outside air (FIG. 6F).

The mass transfer device of this Example was used for experiment of separating polyethylene glycol and tetraethylene glycol in the same manner as in Example 1. With the mass transfer device of this Example, two distinct peaks of the output signal were detected owing to the difference in elution time between polyethylene glycol and tetraethylene glycol.

Example 4

The mass transfer device shown in FIGS. 1A and 1B was used as a micro-reactor for chemical reaction in this Example. The chemical reaction conducted was oxidation of propene $C_3H_6$ to acrolein $C_3H_4O_4$. The reaction catalyst was fine particulate $Cu_2O$.

In this Example, differently from Example 1, in the step of FIG. 2F, a solution containing fine particulate $Cu_2O$ was added dropwise to the portion of the packing material (porous silicon dioxide) formed on the substrate. After sufficient drying, intercepting member 205 was bonded to monocrystalline substrate 201 with an epoxy adhesive in the same manner as in Example 1. Thus, a mass transfer device was produced in which the catalyst $Cu_2O$ is held on the surface of porous silicon dioxide 204.

The mass transfer device produced by the aforementioned process as shown in FIGS. 1A and 1B was used for the chemical reaction. Firstly, the mass transfer device was placed on a hot plate set at a temperature of 370° C. to keep the device at the temperature necessary for the reaction. Then a gaseous mixture of propene and $O_2$ were introduced from inlet 105 by use of $N_2$ gas as the carrier gas. The concentrations of propene and $O_2$ were respectively about 1 vol %. The gas having passed through the flow channel packed with porous silicon dioxide was discharged from outlet 106. The gas discharged from outlet 106 was collected and analyzed by gas chromatography. Thereby formation of acrolein was confirmed. In this Example, the propene and $O_2$ in the gas mixture reacted chemically under a catalytic action of $Cu_2O$ during passage through the flow channel packed with packing material 103.

In this Example, the catalyst was deposited in the packing material by an inkjet method, whereby the catalyst substance was allowed to be supported efficiently and uniformly. Use of the porous packing material gave the high reaction efficiency of the chemical reaction.

The invention claimed is:

1. A process for producing a mass transfer device for transferring a specified substance by flowing a fluid containing the specified substance through a flow channel packed with a packing material on a substrate, comprising the steps of
   (a) preparing a substrate,
   (b) forming a flow channel on a surface side of the substrate,
   (c) applying drops of a liquid into the flow channel from the surface side by energizing the liquid to eject the drops, the liquid comprised of a packing material and a liquid medium, and
   (d) removing the liquid medium to leave the packing material in the flow channel,
   (e) leveling the surface side of the substrate and a surface of the packing material, and
   (f) bonding another substrate on to the substrate to seal the packing material from outside air.

2. The process according to claim 1, wherein the packing material exerts action on the specified substance to differentiate a transfer rate from another specified substance.

3. The process according to claim 1, wherein the packing material exerts action to cause a physical or chemical reaction of the specified substance.

4. The process according to claim 1, wherein the packing material after the step (d) contains a porous material.

5. The process according to claim 4, wherein the porous material contains porous silicon dioxide.

6. The process according to claim 1, wherein the liquid drop is a sol, and in the step (d), the sol is convened to a gel.

7. The process according to claim 1, wherein the step (e) is a step of polishing the packing material.

8. The process according to claim 1, wherein the process comprises, after the step (d), the further step of (f) applying a treating liquid for treating the surface of the packing material.

9. The process according to claim 1, wherein the process comprises, after the step (d), the further step of (g) sealing the packing material from outside air.

* * * * *